United States Patent
Zhang

(10) Patent No.: US 8,026,251 B2
(45) Date of Patent: Sep. 27, 2011

(54) HUPERZINE A AND ITS DERIVATIVES AS ANALGESIC AGENTS

(76) Inventor: Hesheng Zhang, Tianjin (CN)

( * ) Notice: Subject to any disclaimer, the term of this patent is extended or adjusted under 35 U.S.C. 154(b) by 128 days.

(21) Appl. No.: 12/020,520

(22) Filed: Jan. 26, 2008

(65) Prior Publication Data

US 2008/0119506 A1 May 22, 2008

Related U.S. Application Data

(63) Continuation of application No. PCT/CN2005/001468, filed on Sep. 13, 2005.

(30) Foreign Application Priority Data

Aug. 1, 2005 (CN) .......................... 2005 1 0014685

(51) Int. Cl.
*A61K 31/4412* (2006.01)
(52) U.S. Cl. ....................................................... 514/295
(58) Field of Classification Search .................. 514/295
See application file for complete search history.

(56) References Cited

U.S. PATENT DOCUMENTS

2006/0264454 A1* 11/2006 Schachter ..................... 514/291
2009/0048234 A1* 2/2009 Volvovitz ..................... 514/215

OTHER PUBLICATIONS

The Merck Manual [Migraine, The Merck Manual of Diagnosis and Therapy (17th Edition), pp. 1376-1377; 1999].*
Clouse et al. (Gastroenterology; vol. 130, pp. 1492-1497; 2006).*
Morissette et al. (Advanced Drug Delivery Reviews, vol. 56, pp. 275-300; 2004).*
Vippagunta et al. (Advanced Drug Delivery Reviews, vol. 48, Abstract; 2001).*

* cited by examiner

*Primary Examiner* — Phyllis G Spivack
*Assistant Examiner* — Nelson C Blakely, III
(74) *Attorney, Agent, or Firm* — Matthias Scholl P.C.; Matthias Scholl

(57) ABSTRACT

The present invention relates to a method for treating or alleviating migraines, by administering to a patient in need thereof compound (I), or salts thereof, or pharmaceutical preparations thereof comprising mixtures of compound (I) or salts thereof with pharmaceutically-acceptable diluents

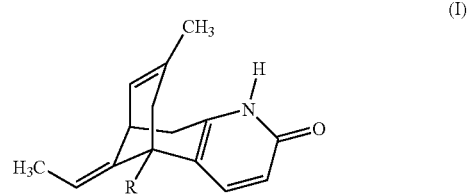

wherein: R represents —NHC(O)OR³; and R³ represents methyl, ethyl, propyl, isopropyl, butyl, isobutyl, tert-butyl or phenylmethyl.

1 Claim, No Drawings

HUPERZINE A AND ITS DERIVATIVES AS ANALGESIC AGENTS

CROSS-REFERENCE TO RELATED APPLICATIONS

This application is a continuation of International Patent Application No. PCT/CN2005/001468 with an international filing date of Sep. 13, 2005, designating the United States, now pending, and further claims priority benefits to Chinese Patent Application No. 200510014685.6, filed Aug. 1, 2005. The contents of the aforementioned specifications are incorporated herein by reference.

BACKGROUND OF THE INVENTION

1. Field of the Invention

This invention relates to huperzine A and its derivatives, as well as their application as pharmaceutically-active analgesic agents.

2. Description of the Related Art

Chronic pain types include cancer pain, caused by the tumor pressing on bones, nerves, and other organs; nociceptive pain, caused by damage of tissues or organs; arthritic pain, caused by autoimmune response, such as inflammation (arthritis, gastritis, hepatitis); and neuropathic pain, especially migraine pain, caused by various abnormalities of the central nervous system.

Clinically, migraine pain features pulsating headache on one or both sides of the head, having duration of between 4 and 74 hours for each attack, and being simultaneously accompanied by symptoms of nausea, vomiting and photophobia. In certain patients specific premonitory symptoms, lasting about 10 to 20 min, such as visual symptoms of scotoma and light flash, numbness, and dizziness, may occur before the incidence of migraines.

With acceleration of the life styles and increase of work pressure, the incidence of migraines has been on the rise throughout the world. In fact, migraines constitute now the most common medical condition distressing modern people. For example, in China migraine affects 3%-5% of adult population, of which females are more susceptible than males by a factor of 3 to 4. In most cases, the onset of migraine occurs in adolescence.

In developed countries, the incidence of migraine is much higher. The statistics from the National Headache Foundation (USA) show that one of every ten people suffers from migraine headaches in USA, but more than half of the patients have not been even properly diagnosed. Similar data from the National Institute of Neurological Disorders and Stroke (NIH, USA) has revealed that there are 28 million patients with migraines in America and that migraine has caused an annual loss of about 157 million working days. Not surprisingly, pain management is one of the most common goals of homeopathy, and the treatment of migraine has become a hot medical field.

Conventional analgesics include two main types: opiate receptor ligands, with the typical example of morphine, which has strong analgesic effects but is prone to cause addiction; and non-narcotic analgesics, with the typical example of aspirin-derived paracetamol. There are also various new-generation analgesics having multiple mechanisms of action, conceived and manufactured successfully via modern processes for drug design, screening and development, which have weak analgesic effects, but which usually do not form dependence. Although some of these analgesics have serious side effects, e.g., they cause damage to the digestive tract, they are widely used and have an estimated combined market share of nearly 10 billion US dollars.

In the past twenty years, new types of 5-hydroxytryptamine (5-HT) antagonists and receptor stimulants have been identified in migraine effective treatment agents. Meanwhile, the development of analgesics acting on various targets of CNS has become a hot field in the new drug development area. However, most of these research objectives have focused on the 5-HT receptor and the dopamine receptor. Specifically, in the last 10 years, it was discovered that the 5-HT receptor and the dopamine receptors are divided into various subtypes, and the ability to interact with certain subtypes is related to analgesic effects of drugs, as well as the decrease or complete elimination of toxic and other side effects. This precipitated a great amount of research on these targets.

Acetylcholine, a neurotransmitter, was discovered much earlier than 5-HT. However, the acetylcholine receptor and acetylcholine esterase have not been popular targets for developing analgesic drugs. Nevertheless, in European Pat. No. EP 413667 A and U.S. Pat. No. 5,010,083, compounds used for treatment of both memory loss and relief of pain have been reported, which suggests that improvement of memory has some association with analgesia, and further reveals that increase in the level of acetylcholine may have analgesic action.

In addition, Stoyan once reported that the alkaloids nivalin and syntostigmine may alleviate migraine pain (Stoyan Iv Ikonomoff, Archives Suisses de Neurologie, Neurochirurgie et de Psychiatrie, Vol. 102, Fascicule, pages 299-312 (1968)). It was later found that these two compounds may inhibit activity of acetylcholine esterase. Because of a low inhibition activity of acetylcholine esterase or a low ability to permeate the blood-brain barrier, higher doses of these two compounds, and other acetylcholine esterase inhibitors subsequently tested, are required in order to provide therapeutic effects.

To achieve high concentrations, these compounds must be administered by injection. Hence, on one hand, the blood drug concentration is so high so as to have many side effects; on the other hand, the administration by way of injection is inconvenient. As a result, the research on acetylcholine esterase inhibitors used for treatment of migraine was put on hold. This was the first time when it was proposed that acetylcholine esterase inhibitors could be used for treatment of migraine.

The breakthrough in this field came from research and development of novel inhibitors of acetylcholine esterase. These novel inhibitors, such as donepezil, have high activity, highly-selectivity and easy permeation through the blood-brain barrier, so that they are able to overcome the shortcomings of the first generation of acetylcholine esterase inhibitors described above for the treatment of migraine. As disclosed in U.S. Pat. No. 6,608,088, donepezil was observed to have efficacy on migraine in clinical trials.

Huperzine A can inhibit acetylcholine esterase selectively, is easy to permeate through the blood-brain barrier, can promote memory reappearance and enhance memory maintenance. However, no literature reports have appeared that huperzine A may used for pain control, and especially the treatment of migraine.

SUMMARY OF THE INVENTION

Promoting function of acetylcholine as a nervous transmitter is a reliable new pharmacological mechanism for analgesia. Novel inhibitors of acetylcholine esterase, with high activity, highly selective inhibition of the central acetylcholine esterase, easy permeation through the blood-brain barrier, long duration and convenient administration, provide a breakthrough for pain control, especially for treatment of migraine.

Through animal experiments, we found that huperzine A and its derivatives have a much higher efficacy than donepezil. Specifically, we have found in clinical studies that oral huperzine A alleviates and/or cures migraine, and that long-term administration of huperzine A prevents migraine attacks.

In certain embodiments of the present invention, provided is a method for treating pain, functional pain syndrome or organic pain syndrome comprising administering to a patient in need thereof a compound of formula (I) or the salts thereof to alleviate or treat pain, functional pain syndrome or organic pain syndrome in mammals,

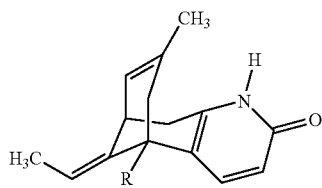
(I)

wherein: R represents —$NR^1R^2$, —$NHC(O)OR^3$, —$N=CR^4R^5$; $R^1$ represents H or $C_{1-6}$alkyl; $R^2$ represents H or $C_{1-6}$alkyl; $R^3$ represents $C_{1-6}$alkyl, a heterocyclic group or an aryl; $R^4$ represents H, $C_{1-6}$ alkyl, a heterocyclic group or an aryl; and $R^5$ represents H, $C_{1-6}$alkyl, a heterocyclic group or an aryl; or $CR^4R^5$ taken together represents a cyclolidene group.

DETAILED DESCRIPTION OF THE INVENTION

The present invention relates to a method for treating, alleviating, or preventing pain, particularly migraines, functional pain syndrome, or organic pain syndrome, comprising administering to a patient in need thereof a compound of formula (I), or salts thereof, or pharmaceutical preparations thereof comprising mixtures of a compound of formula (I) or salts thereof with pharmaceutically-acceptable diluents

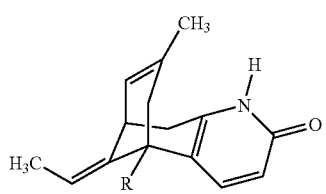
(I)

wherein: R represents —$NR^1R^2$, —$NHC(O)OR^3$, —$N=CR^4R^5$; $R^1$ represents H or $C_{1-6}$ alkyl; $R^2$ represents H or $C_{1-6}$ alkyl; $R^3$ represents $C_{1-6}$ alkyl, a heterocyclic group or an aryl; $R^4$ represents H, $C_{1-6}$ alkyl, a heterocyclic group or an aryl; and $R^5$ represents H, $C_{1-6}$ alkyl, a heterocyclic group or an aryl; or $CR^4R^5$ taken together represents a cyclolidene group.

When representing $C_{1-6}$alkyl, $R^1$, $R^2$, $R^3$, $R^4$, or $R^5$ may be linear chain alkyl, fork chain alkyl, or cyclic chain alkyl; may be saturated or unsaturated chain alkyl, and may be substituted by one or more fluorine, hydroxyl, alkoxyl, ester group, amidocyanogen, amido, and carboxyl.

When $R^1$, $R^2$, $R^3$, $R^4$, or $R^5$ represent a heterocyclic group, $R^1$, $R^2$, $R^3$, $R^4$, or $R^5$ may be a pentacycle, a hexacycle, a heptacycle or an octocycle; may be saturated or unsaturated cycle; may contain one or more oxygen, nitrogen or sulfur atoms; and may be substituted by one or more fluorine, hydroxyl, alkoxyl, ester group, amidocyanogen, amido, or carboxyl.

When $R^1$, $R^2$, $R^3$, $R^4$, or $R^5$ represent an aryl group, $R^1$, $R^2$, $R^3$, $R^4$, or $R^5$ may be a five-membered or a six-membered aryl group; may be an one-cycle or a two-cycle aryl group; may contain one or more than one oxygen, nitrogen or sulfur atoms; and may be substituted by one or more than one fluorine, hydroxyl, alkoxyl, ester group, amidocyanogen, amido, or carboxyl group.

When R represents $N=CR^4R^5$, a compound of formula (I) may be an E-isomer, Z-isomer or mixture of an E-isomer and a Z-isomer.

Among compounds represented by formula (I), suitable as a pharmaceutically-active ingredient for the treatment of pain, functional pain syndrome or organic pain syndrome, are compounds containing R which represents —$NR^1R^2$, wherein, $R^1$, and $R^2$ represent independently and at each occurrence hydrogen, methyl, ethyl, propyl, isopropyl or butyl; particularly suitable as a pharmaceutically active ingredient for treatment of pain, functional pain syndrome or organic pain syndrome, are compounds containing R which represents —$NR^1R^2$, wherein, $R^1$, and $R^2$ represent independently and at each occurrence hydrogen, methyl, ethyl, or propyl; and most particularly suitable as a pharmaceutically active ingredient for treatment of pain, functional pain syndrome or organic pain syndrome, are compounds containing R which represents $NR^1R^2$, wherein, $R^1$, and $R^2$ represent hydrogen, or methyl.

Among compounds represented by formula (I), suitable as a pharmaceutically active ingredient for treatment of pain, functional pain syndrome or organic pain syndrome, are compounds containing R which represents —$NHC(O)OR^3$, wherein, $R^3$ represents independently and at each occurrence methyl, ethyl, propyl, isopropyl, butyl, isobutyl, tert-butyl, neo-butyl, 1-pentyl, 1-methylbutyl, 2-methylbutyl, 3-methylbutyl, 1,1,-dimethylpropyl, 2,2-dimethylpropyl, 1,2-dimethylpropyl, cyclopentyl, cyclohexyl, hexyl, phenyl, 2-Cl-phenyl, 3-Cl-phenyl, 4-Cl-phenyl, 2-OH-phenyl, 3-OH-phenyl, 4-OH-phenyl, 2-aminophenyl, 3-aminophenyl, 4-aminophenyl, 2-methylaminophenyl, 3-methylaminophenyl, 4-methylaminophenyl, 2-methylphenyl, 3-methylphenyl, 4-methylphenyl, 2-methoxylphenyl, 3-methoxylphenyl, 4-methoxylphenyl, 2-fluorophenyl, 3-fluorophenyl, 4-fluorophenyl, 2-pyridyl, 3-pyridyl, 4-pyridyl, or phenylmethyl; particularly suitable as a pharmaceutically active ingredient for treatment of pain, functional pain syndrome or organic pain syndrome, are compounds containing R which represents —$NHC(O)OR^3$, wherein, $R^3$ represent methyl, ethyl, propyl, isopropyl, butyl, tert-butyl, phenyl, 2-Cl-phenyl, 3-Cl-phenyl, 4-Cl-phenyl, 2-OH-phenyl, 3-OH-phenyl, 4-OH-phenyl, 2-dimethylaminophenyl, 3-dimethylaminophenyl, 4-dimethylaminophenyl, 2-methylphenyl, 3-methylphenyl, 4-methylphenyl, 2-methoxylphenyl, 3-methoxylphenyl, 4-methoxylphenyl, 2-fluorophenyl, 3-fluorophenyl, 4-fluorophenyl, 2-pyridyl, 3-pyridyl, 4-pyridyl, or phenylmethyl; and most particularly suitable as a pharmaceutically active ingredient for treatment of pain, functional pain syndrome or organic pain syndrome, are compounds containing R which represents —$NHC(O)OR^3$, wherein, $R^3$ represent ethyl, propyl isopropyl, butyl, tert-butyl, phenyl, or benzyl group.

Among compounds represented by formula (I), suitable as a pharmaceutically active ingredient for treatment of pain, functional pain syndrome or organic pain syndrome, are compounds containing R which represents —N=CR$^4$R$^5$, wherein, R$^4$, R$^5$ represent independently and at each occurrence hydrogen, methyl, ethyl, propyl, isopropyl, butyl, isobutyl, tert-butyl, neo-butyl, 1-pentyl, 1-methylbutyl, 2-methylbutyl, 3-methylbutyl, 1,1-dimethylpropyl, 2,2-dimethylpropyl, 1,2-dimethylpropyl, cyclopentyl, cyclohexyl, hexyl, phenyl, 2-Cl-phenyl, 3-Cl-phenyl, 4-Cl-phenyl, 2-OH-phenyl, 3-OH-phenyl, 4-OH-phenyl, 3,4-dihydroxylphenyl, 3-OH-4-($C_{1-5}$-alkyloxyl)phenyl, 3-($C_{1-5}$-alkyloxyl)-4-($C_{1-5}$-alkyloxyl)phenyl, 2-aminophenyl, 3-aminophenyl, 4-aminophenyl, 2-methylaminophenyl, 3-methylaminophenyl, 4-methylaminophenyl, 2-dimethylaminophenyl, 3-dimethylaminophenyl, 4-dimethylaminophenyl, 2-methylphenyl, 3-methylphenyl, 4-methylphenyl, 2-methoxylphenyl, 3-methoxylphenyl, 4-methoxylphenyl, 2-fluorophenyl, 3-fluorophenyl, 4-fluorophenyl, 2-thienyl, 3-thienyl, 2-furanyl, 3-furanyl, 2-pyridyl, 3-pyridyl, 4-pyridyl, or benzyl; particularly suitable as a pharmaceutically active ingredient for treatment of pain, functional pain syndrome or organic pain syndrome, are compounds containing R which represents —N=CR$^4$R$^5$, wherein, R$^4$, and R$^5$ represent independently and at each occurrence hydrogen, methyl, ethyl, propyl, isopropyl, butyl, isobutyl, tert-butyl, neo-butyl, cyclopentyl, cyclohexyl, hexyl, phenyl, 2-Cl-phenyl, 3-Cl-phenyl, 4-Cl-phenyl, 2-OH-phenyl, 3-OH-phenyl, 4-OH-phenyl, 3,4-dihydroxylphenyl, 3-OH-4-methoxylphenyl, 3-methoxyl-4-methoxylphenyl, 2-methylphenyl, 3-methylphenyl, 4-methylphenyl, 2-methoxylphenyl, 3-methoxylphenyl, 4-methoxylphenyl, 2-fluorophenyl, 3-fluorophenyl, 4-fluorophenyl, 2-pyridyl, 3-pyridyl, or 4-pyridyl; and most particularly suitable as a pharmaceutically active ingredient for treatment of pain, functional pain syndrome or organic pain syndrome, are compounds containing R which represents —N=CR$^4$R$^5$, wherein, R$^4$, and R$^5$, represent independently and at each occurrence hydrogen, methyl, ethyl, propyl, isopropyl, butyl, cyclohexyl, phenyl, 3-OH-4-methoxylphenyl, 3-hydroxylphenyl, 4-methoxylphenyl, 3-fluorophenyl, or 4-pyridyl.

The compounds represented by formula (I) to be used for treatment of pain, functional pain syndrome or organic pain syndrome, and various pharmaceutically-acceptable inorganic acid salts or organic acid salts thereof are administered at a dose of between 0.001 and 500 mg per administration; more particularly, at a dose of between 0.01 and 100 mg per administration, and most particularly at a dose of between 0.05 and 50 mg per administration. Single or multiple daily administrations may be necessary. Particularly, the compound may be administered once, twice, three times, or four times per day, or at a different dosing interval, e.g., as ordered by a physician.

This invention relates also to pharmaceutical compositions comprising a compound represented by formula (I), and a carrier, filler, solvent, diluter, colorant, and/or adhesive. The proportion of the compound represented by formula (I) to a carrier, filler, solvent, diluter, colorant, and/or adhesive depends on the mode of administration. Modes of administration include those through the gastrointestinal tract, the oral cavity, the vein, the endodermis, the muscle injection, the nasal cavity, the eye, inhalation, the anus, the vaginal tract, the percutaneous absorption, and other ways.

The pharmaceutical composition of the present invention may also be prepared as a control-release agent.

The pharmaceutical composition of the present invention may also comprise other pharmaceutically-active ingredients, including e.g., other pharmaceutically-active ingredients used heretofore to alleviate pain, including migraines.

The pain meant to be treated, alleviated, or prevented by compounds and methods of the present invention includes all distress resulting from pain, functional pain syndrome, or organic pain syndrome, including but not limited to nervous headache, especially migraine, primary fibromylgia, amputation resulting from fracture trauma, tumoral denervation resulting from damage to nerves caused by tumor, traumatic denervation resulting from nervous injury, or pain resulting from pathological damage of autoimmune mechanism.

EXAMPLES

Example 1

(5R,9R,11E)-5-amino-11-ethylidene-5,6,9,10-tetrahydro-7-methyl-5,9-methanocycloocta[b]pyridin-2(1H)-one (Huperzine A), was purchased from the Institute of Poisons and Drugs, Chinese Academy of Military Medical Sciences.

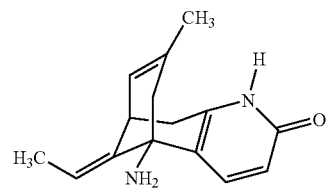

Example 2

(5R,9R,11E)-5-methylamino-11-ethylidene-5,6,9,10-tetrahydro-7-methyl-5,9-methanocycloocta[b]pyridin-2(1H)-one

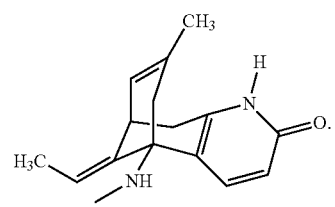

Huperzine A 10 mg, and 37% aqueous solution of formaldehyde were refluxed for 1 hour in 2 mL of isopropanol; the solvent was stripped in vacuo; THF (dry, 5 mL) and NaBH(OOCCH$_3$)$_3$ 0.15 g were added, the reaction mixture was allowed to stir for 4 hours; and then filtered to remove solid substances. The filtrate was purified after concentrating on prep TLC (chloroform:methanol=9:1) to yield 6 mg of pure title compound. MS: 257 (M+1).

Example 3

(5R,9R,11E)-5-dimethylamino-11-ethylidene-5,6,9,10-tetrahydro-7-methyl-5,9-methanocycloocta[b]pyridin-2(1H)-one

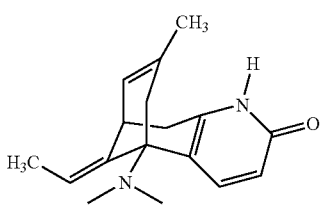

The title compound was prepared as described in Example 2, except that huperzine A was replaced with (5R,9R,11E)-5-dimethylamino-1,1-ethylidene-5,6,9,10-tetrahydro-7-methyl-5,9-methanocycloocta[b]pyridin-2(1H)-one. MS: 271(M+1).

Example 4

(5R,9R,11E)-5-ethylamino-11-ethylidene-5,6,9,10-tetrahydro-7-methyl-5,9-methanocycloocta[b]pyridin-2(1H)-one

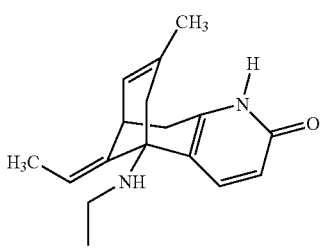

The title compound was prepared as described in Example 2, except that formaldehyde was replaced with acetaldehyde. MS: 271 (M+1).

Example 5

(5R,9R,11E)-5-butylamino-11-ethylidene-5,6,9,10-tetrahydro-7-methyl-5,9-methanocycloocta[b]pyridin-2(1H)-one

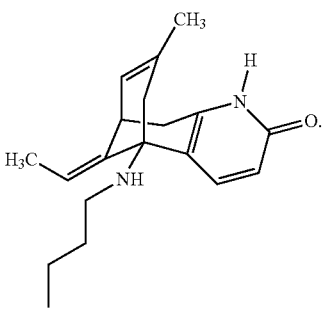

The title compound was prepared as described in Example 2, except that formaldehyde was replaced with butyraldehyde. MS: 299 (M+1).

Example 6

(5R,9R,11E)-5-(ethoxycarbonylamino)-11-ethylidene-5,6,9,10-tetrahydro-7-methyl-5,9-methanocycloocta[b]pyridin-2(1H)-one

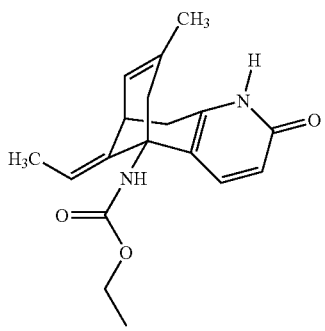

Dissolved 10 mg huperzine A and 10 mg triethylamine in 5 mL dry THF; cooled the solution down to 0° C.; added ethyl chlorocarbonate (6 mg) and stirred the resultant reaction mixture for 4 hours; filtered to remove solid residues; after concentrating the filtrate, purified on prep TLC (chloroform:methanol=9:1) to yield 8 mg of pure title compound. MS: 315 (M+1).

Example 7

(5R,9R,11E)-5-(2-methylpropoxycarbonylamino)-11-ethylidene-5,6,9,10-tetrahydro-7-methyl-5,9-methanocycloocta[b]pyridin-2(1H)-one

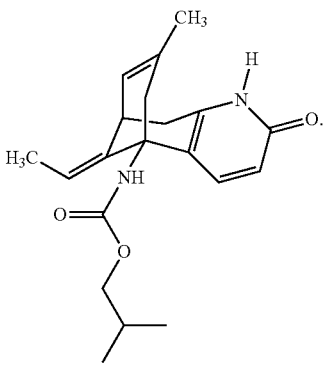

The title compound was prepared as described in Example 6, except that ethyl chlorocarbonate was replaced with isobutyl chlorocarbonate.

Example 8

(5R,9R,11E)-5-(tert-butoxycarbonylamino)-1,1-ethylidene-5,6,9,10-tetrahydro-7-methyl-5,9-methanocycloocta[b]pyridin-2(1H)-one

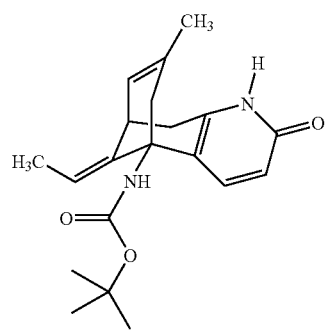

The title compound was prepared as described in Example 6, except that ethyl chlorocarbonate was replaced with tert-butyl chlorocarbonate.

Example 9

(5R,9R,11E)-5-(benzyloxycarbonylamino)-11-ethylidene-5,6,9,10-tetrahydro-7-methyl-5,9-methanocycloocta[b]pyridin-2(1H)-one

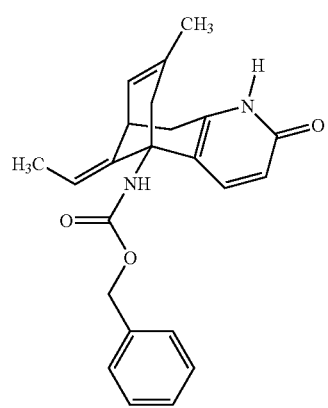

The title compound was prepared as described in Example 6, except that ethyl chlorocarbonate was replaced with methyl benzyl chlorocarbonate.

Example 10

(5R,9R,11E)-5-(4-hydroxy-3-methoxyphenylmethylidenylamino)-11-ethylidene-5,6,9,10-tetrahydro-7-methyl-5,9-methanocycloocta[b]pyridin-2(1H)-one

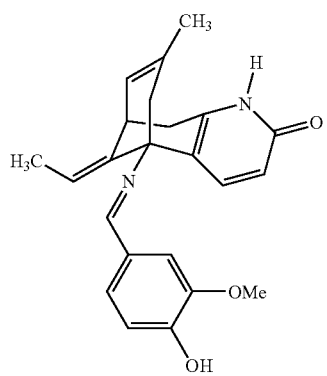

Added 10 mg huperzine A and 8 mg vanillin in 5 mL isopropanol; stirred at reflux for 3 hours; stripped solvent in vacuo to yield 16 mg product. MS: 377 (M+1).

Example 11

(5R,9R,11E)-5-(3-hydroxy-4-methoxyphenylmethylidenylamino)-11-ethylidene-5, 6, 9, 10-tetrahydro-7-methyl-5,9-methanocycloocta[b]pyridin-2(1H)-one

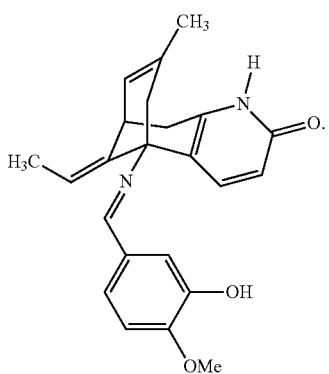

The title compound was prepared as described in Example 10, except that vanillin was replaced with isovanillin. MS: 377 (M+1).

Example 12

(5R,9R,11E)-5-phenylmethylidenylamino-11-ethylidene-5,6,9,10-tetrahydro-7-methyl-5,9-methano-cycloocta[b]pyridin-2(1H)-one

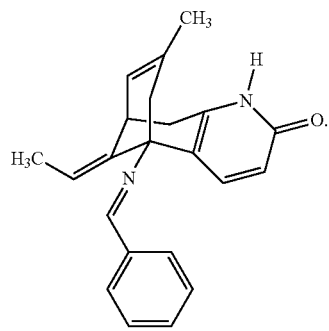

The title compound was prepared as described in Example 10, except that vanillin was replaced with benzaldehyde. MS: 331 (M+1).

Example 13

(5R,9R,11E)-5-(4-pyridinylmethylidenylamino)-11-ethylidene-5,6,9,10-tetrahydro-7-methyl-5,9-methanocycloocta[b]pyridin-2(1H)-one

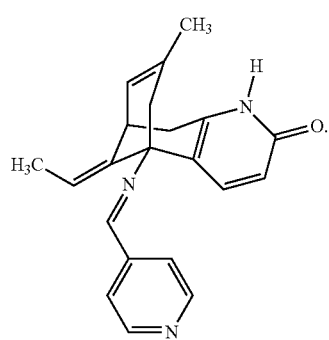

The title compound was prepared as described in Example 10, except that vanillin was replaced with 4-pyridylaldehyde. MS: 332 (M+1).

Example 14

(5R,9R,11E)-5-(cyclohexanylidenylamino)-11-ethylidene-5,6,9,10-tetrahydro-7-methyl-5,9-methano-cycloocta[b]pyridin-2(1H)-one

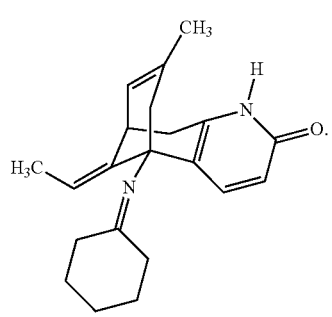

The title compound was prepared as described in Example 10, except that vanillin was replaced with cyclohexanone. MS: 323 (M+1).

Example 15

(5R,9R,11E)-5-(1-methylpiperidin-4-ylidenylamino)-11-ethylidene-5,6,9,10-tetrahydro-7-methyl-5,9-methanocycloocta[b]pyridin-2(1H)-one

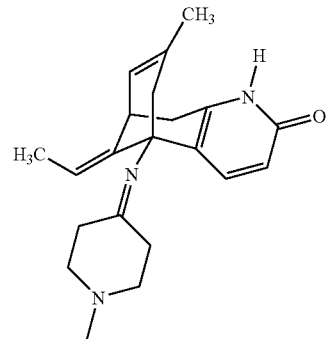

The title compound was prepared as described in Example 10, except that vanillin was replaced with 1-methyl-4-piperidone. MS: 338 (M+1).

Example 16

(5R,9R,11E)-5-(cyclohexanylmethylidenylamino)-11-ethylidene-5,6,9,10-tetrahydro-7-methyl-5,9-methanocycloocta[b]pyridin-2(1H)-one

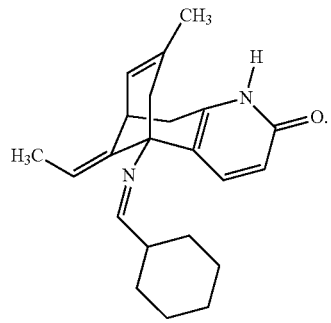

The title compound was prepared as described in Example 10, except that vanillin was replaced with cyclohexylaldehyde.

Example 17

(5R,9R,11E)-5-(2-butylidenylamino)-11-ethylidene-5,6,9,10-tetrahydro-7-methyl-5,9-methanocycloocta[b]pyridin-2(1H)-one

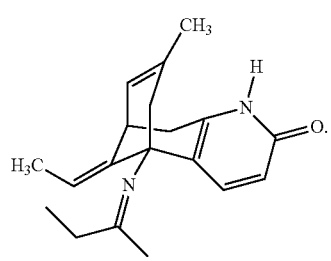

The title compound was prepared as described in Example 10, except that vanillin was replaced with butanone.

Example 18

(5R,9R,11E)-5-(1-butylidenylamino)-11-ethylidene-5,6,9,10-tetrahydro-7-methyl-5,9-methanocycloocta[b]pyridin-2(1H)-one

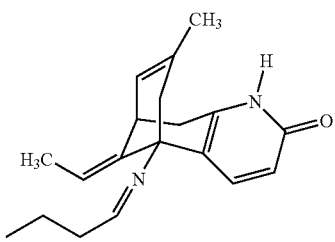

The title compound was prepared as described in Example 10, except that vanillin was replaced with butyraldehyde.

Example 19

(5R,9R,11E)-5-(4-methoxyphenylmethylidenylamino)-11-ethylidene-5,6,9,10-tetrahydro-7-methyl-5,9-methanocycloocta[b]pyridin-2(1H)-one

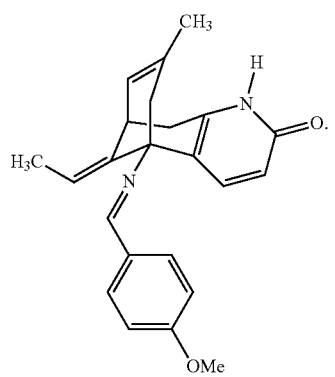

The title compound was prepared as described in Example 10, except that vanillin was replaced with 4-methoxybenzaldehyde. MS: 361 (M+1).

Example 20

(5R,9R,11E)-5-(3-hydroxyphenylmethylidenylamino)-11-ethylidene-5,6,9,10-tetrahydro-7-methyl-5,9-methanocycloocta[b]pyridin-2(1H)-one

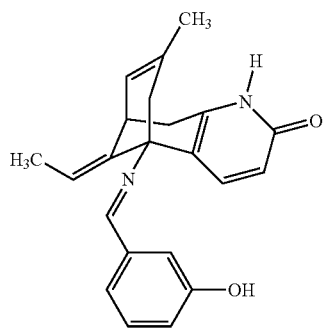

The title compound was prepared as described in Example 10, except that vanillin was replaced with 3-hydroxybenzaldehyde. MS: 347 (M+1).

Example 21

(5R,9R,11E)-5-(3-fluorophenylmethylidenylamino)-11-ethylidene-5,6,9,10-tetrahydro-7-methyl-5,9-methanocycloocta[b]pyridin-2(1H)-one

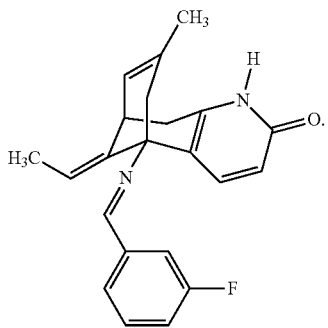

The title compound was prepared as described in Example 10, except that vanillin was replaced with 3-fluorobenzaldehyde. MS: 349 (M+1).

Animal Tests

Test 1: Hot Plate Test

1. Test Materials 1.1 Animals

Kunming mice, grade 2, female, weight of 20±2 g, purchased from the Division of Laboratory Animals, Department of Medical Sciences of Peking University, animal license No.: SCX Jing 2002-0001.

1.2 Drugs 1.2.1 Solutions of huperzine A and huperzine A derivatives in normal saline water were prepared for stomach perfusion of mice.

1.2.2 Solutions of bucinnazine hydrochloride tablets, 30 mg/tablet, manufactured by Tianjin Lisheng Pharmaceutical Factory, approval No.: 0201001, in normal saline solution were prepared at a concentration of 1.5 mg/ml for stomach perfusion of mice.

2. Methods

A water bath was heated to a constant temperature of 55±0.5° C. The bottom of a metal plate was placed in contact with water surface. A mouse was placed on the hot plate and a timer was activated. The timer was deactivated when the mouse began licking its rear feet. The measured time was taken as the pain threshold. The pain threshold was measured two times for each mouse, and those mice whose average pain threshold was less than 30 s were qualified for the experiment.

Qualified mice were randomly divided into groups of 10. At first the pain threshold before administration of a drug was measured. Then drugs were administered as identified in Table 1. The administration volume was 0.2 ml per each 10 g of weight. Normal saline solution was administered to the control group. After administration, the pain threshold was measured at different time periods post-administration. A statistical t-test was calculated of the group interval, based on the test data.

3. Results

The results are shown as Table 1.

TABLE 1

Effect of drugs on the pain thresholds for mice in a hot plate test (x ± s, n = 10)

| Groups | Dose mg/kg | Pain thresholds before administration(s) | Pain Thresholds in Different Periods after Administration(s) | | | | |
|---|---|---|---|---|---|---|---|
| | | | at 30 min | at 60 min | at 120 min | at 180 min | at 240 min |
| Control | — | 16.2 ± 2.79 | 13.7 ± 3.53 | 14.8 ± 4.41 | 14.5 ± 3.27 | 14.7 ± 2.98 | 14.7 ± 2.71 |
| Huperzine A | 0.2 | 14.2 ± 4.49 | 13.3 ± 4.05 | 14.5 ± 5.08 | 14.2 ± 5.20 | 13.3 ± 3.68 | 14.6 ± 2.84 |
| Huperzine A | 0.4 | 15.3 ± 2.86 | 28.4 ± 8.12 *** | 31.7 ± 10.56 *** | 27.6 ± 8.22 *** | 25.5 ± 8.88 ** | 27.8 ± 5.94 *** |

TABLE 1-continued

Effect of drugs on the pain thresholds for mice in a hot plate test (x ± s, n = 10)

| Groups | Dose mg/kg | Pain thresholds before adminis- tration(s) | Pain Thresholds in Different Periods after Administration(s) | | | | |
|---|---|---|---|---|---|---|---|
| | | | at 30 min | at 60 min | at 120 min | at 180 min | at 240 min |
| Compound of Example 7 | 0.6 | 15.8 ± 3.97 | 28.5 ± 2.55 ** | 30.1 ± 6.90 *** | 27.7 ± 4.49 *** | 23.1 ± 2.41 ** | |
| Compound of Example 10 | 0.6 | 16.9 ± 2.77 | 26.2 ± 5.94 ** | 32.8 ± 7.36 *** | 29.6 ± 6.60 *** | 25.8 ± 1.84 ** | |

Notes:
By comparing with the control group,
* $p < 0.05$;
** $p < 0.01$;
*** $p < 0.001$ Test 2: Treatment of Migraine with Oral Huperzine A Drug: Huperzine A Tablet (50 μg/tablet, manufactured by Henan Zhulin Zhongsheng Pharmaceutical Factory.)

Case 1:

Patient: Female, 38-year old, with a medical history of migraine of 5 years, exhibiting nausea during attacks of migraine, and occasionally vomiting. Previously treated with bufferin plus, but recently reported that analgesic effects of bufferin plus have weakened.

Methods: On occurrence of migraine pains (8 times within a month), two tablets of huperzine A were administered. Within 20 minutes from administration, the headache has completely disappeared. Minor side effects were observed. Good analgesic effects were reported over a period of one month Case 2

Patient: Female, 41-year old, with a medical history of migraine of 2 years. Previously treated with ergotamine, but recently reported that analgesic effects of ergotamine have weakened.

Methods: On occurrence of migraine pains (10 times within a month), two tablets of huperzine A were administered. Within 30 minutes from administration, the headache has completely disappeared. No side effects were observed. Good analgesic effects were reported over a period of one month Case 3

Patient: Female, 41-year old, with a medical history of migraine of 3 years, occurring at a frequency of about 8-12 times per month.

Methods: One tablet of huperzine A was administered per day orally. The patient did not complain of migraine attacks over the period of 1 month.

What is claimed is:

1. A method for treating or alleviating migraines comprising administering to a patient in need thereof a compound of the formula (I), or its salt,

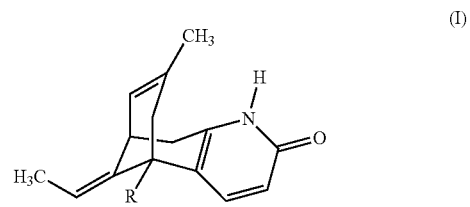

wherein
R represents —NHC(O)OR$^3$; and
R$^3$ represents methyl, ethyl, propyl, isopropyl, butyl, isobutyl, tert-butyl, or phenylmethyl.

* * * * *